United States Patent
DeFreitas et al.

(10) Patent No.: US 11,701,199 B2
(45) Date of Patent: *Jul. 18, 2023

(54) NEEDLE BREAST BIOPSY SYSTEM AND METHOD OF USE

(71) Applicant: Hologic, Inc., Marlborough, MA (US)

(72) Inventors: Kenneth DeFreitas, Patterson, NY (US); Ian Shaw, Yorktown Heights, NY (US); John LaViola, Orange, CT (US); Kathleen Pickett, Uncasville, CT (US); Nikolaos A. Gkanatsios, Danbury, CT (US); Aaron Fand, Bethel, CT (US); Christopher Ruth, Boxford, MA (US)

(73) Assignee: Hologic, Inc., Marlborough, MA (US)

( * ) Notice: Subject to any disclaimer, the term of this patent is extended or adjusted under 35 U.S.C. 154(b) by 437 days.

This patent is subject to a terminal disclaimer.

(21) Appl. No.: 16/809,355

(22) Filed: Mar. 4, 2020

(65) Prior Publication Data

US 2020/0205928 A1   Jul. 2, 2020

Related U.S. Application Data

(63) Continuation of application No. 12/715,591, filed on Mar. 2, 2010, now Pat. No. 10,595,954.

(Continued)

(51) Int. Cl.
*A61B 90/17* (2016.01)
*A61B 90/11* (2016.01)
(Continued)

(52) U.S. Cl.
CPC ............... *A61B 90/17* (2016.02); *A61B 6/12* (2013.01); *A61B 10/0233* (2013.01);
(Continued)

(58) Field of Classification Search
None
See application file for complete search history.

(56) References Cited

U.S. PATENT DOCUMENTS

| 3,502,878 A | 3/1970 | Stewart |
| 3,863,073 A | 1/1975 | Wagner |

(Continued)

FOREIGN PATENT DOCUMENTS

| AU | 2014339982 | 4/2015 |
| CN | 1846622 | 10/2006 |

(Continued)

OTHER PUBLICATIONS

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

(Continued)

*Primary Examiner* — Jonathan Cwern
(74) *Attorney, Agent, or Firm* — Merchant & Gould P.C.

(57) ABSTRACT

A tilted needle biopsy assembly is provided for mounting on an x-ray system. Because the biopsy needle is angled relative to at least one of the detector and the x-ray source, x-ray imaging may be performed during the biopsy procedure without interference by the biopsy device. The angled biopsy needle additionally allows improved access to the axilla and chest wall of the patient. The stereotactic biopsy device of the present invention may be coupled to any x-ray system, whether upright or prone, including but not limited to mammography systems, tomosynthesis systems, and combination mammography/tomosynthesis systems. The system flexibly supports the use of any mode of image capture (i.e., scout, two dimensional mammogram, three-dimensional reconstructed volume) for either or both target visualization and target localization. With such an arrange- (Continued)

ment, a needle biopsy assembly having improved patient coverage is provided for use with a variety of different x-ray imaging platforms.

18 Claims, 15 Drawing Sheets

Related U.S. Application Data

(60) Provisional application No. 61/249,772, filed on Oct. 8, 2009.

(51) Int. Cl.
  *A61B 10/02* (2006.01)
  *A61B 6/12* (2006.01)
  *A61B 17/34* (2006.01)
  *A61B 6/00* (2006.01)
  *A61B 90/00* (2016.01)
  *A61B 34/00* (2016.01)

(52) U.S. Cl.
  CPC .............. *A61B 90/11* (2016.02); *A61B 6/502* (2013.01); *A61B 34/25* (2016.02); *A61B 2017/3409* (2013.01); *A61B 2090/376* (2016.02)

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,668,889 A | 9/1997 | Hara |
| 5,671,288 A | 9/1997 | Wilhelm et al. |
| 5,712,890 A | 1/1998 | Spivey |
| 5,719,952 A | 2/1998 | Rooks |
| 5,735,264 A | 4/1998 | Siczek et al. |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 | 1/2004 | Zhao |
| 6,744,848 B2 | 6/2004 | Stanton |

(56) References Cited

U.S. PATENT DOCUMENTS

| | | |
|---|---|---|
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 * | 3/2020 | DeFreitas ............... A61B 90/17 |
| 10,624,598 B2 | 4/2020 | Chen |
| 10,977,863 B2 | 4/2021 | Chen |
| 10,978,026 B2 | 4/2021 | Kreeger |
| 11,419,565 B2 | 8/2022 | Gkanatsios |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0047636 A1 | 3/2005 | Gines et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |

(56) References Cited

U.S. PATENT DOCUMENTS

| | | |
|---|---|---|
| 2005/0135555 A1 | 6/2005 | Claus |
| 2005/0135664 A1 | 6/2005 | Kaufhold |
| 2005/0226375 A1 | 10/2005 | Eberhard |
| 2006/0009693 A1 | 1/2006 | Hanover et al. |
| 2006/0018526 A1 | 1/2006 | Avinash |
| 2006/0025680 A1 | 2/2006 | Jeune-Iomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0155209 A1 | 6/2006 | Miller et al. |
| 2006/0147099 A1 | 7/2006 | Marshall et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0291618 A1 | 12/2006 | Eberhard et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas |
| 2009/0005668 A1 | 1/2009 | West et al. |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166267 A1 | 7/2010 | Zhang |
| 2010/0195882 A1 | 8/2010 | Ren et al. |
| 2010/0208037 A1 | 8/2010 | Sendai |
| 2010/0231522 A1 | 9/2010 | Li |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110576 A1 | 5/2011 | Kreeger |
| 2011/0150447 A1 | 6/2011 | Li |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014504 A1 | 1/2012 | Jang |
| 2012/0014578 A1 | 1/2012 | Karssemeijer |
| 2012/0069951 A1 | 3/2012 | Toba |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0189092 A1 | 7/2012 | Jerebko |
| 2012/0194425 A1 | 8/2012 | Buelow |
| 2012/0238870 A1 | 9/2012 | Smith et al. |
| 2012/0293511 A1 | 11/2012 | Mertelmeier |
| 2013/0022165 A1 | 1/2013 | Jang |
| 2013/0044861 A1 | 2/2013 | Muller |
| 2013/0059758 A1 | 3/2013 | Haick |
| 2013/0108138 A1 | 5/2013 | Nakayama |
| 2013/0121569 A1 | 5/2013 | Yadav |
| 2013/0121618 A1 | 5/2013 | Yadav |
| 2013/0202168 A1 | 8/2013 | Jerebko |
| 2013/0259193 A1 | 10/2013 | Packard |
| 2014/0033126 A1 | 1/2014 | Kreeger |
| 2014/0035811 A1 | 2/2014 | Guehring |
| 2014/0064444 A1 | 3/2014 | Oh |
| 2014/0073913 A1 | 3/2014 | DeFreitas et al. |
| 2014/0219534 A1 | 8/2014 | Wiemker et al. |
| 2014/0219548 A1 | 8/2014 | Wels |
| 2014/0327702 A1 | 11/2014 | Kreeger et al. |
| 2014/0328517 A1 | 11/2014 | Gluncic |
| 2015/0052471 A1 | 2/2015 | Chen |
| 2015/0061582 A1 | 4/2015 | Smith |
| 2015/0238148 A1 | 8/2015 | Georgescu |
| 2015/0302146 A1 | 10/2015 | Marshall |
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1 | 2/2016 | Chen |

(56) References Cited

U.S. PATENT DOCUMENTS

| | | |
|---|---|---|
| 2016/0078645 A1 | 3/2016 | Abdurahman |
| 2016/0140749 A1 | 5/2016 | Erhard |
| 2016/0228034 A1 | 8/2016 | Gluncic |
| 2016/0235380 A1 | 8/2016 | Smith |
| 2016/0367210 A1 | 12/2016 | Gkanatsios |
| 2017/0071562 A1 | 3/2017 | Suzuki |
| 2017/0262737 A1 | 9/2017 | Rabinovich |
| 2018/0047211 A1 | 2/2018 | Chen et al. |
| 2018/0137385 A1 | 5/2018 | Ren |
| 2018/0144244 A1 | 5/2018 | Masoud |
| 2018/0256118 A1 | 9/2018 | DeFreitas |
| 2019/0015173 A1 | 1/2019 | DeFreitas |
| 2019/0043456 A1 | 2/2019 | Kreeger |
| 2019/0290221 A1 | 9/2019 | Smith |
| 2020/0046303 A1 | 2/2020 | DeFreitas |
| 2020/0093562 A1 | 3/2020 | DeFreitas |
| 2020/0184262 A1 | 6/2020 | Chui |
| 2020/0253573 A1 | 8/2020 | Gkanatsios |
| 2020/0345320 A1 | 11/2020 | Chen |
| 2021/0100518 A1 | 4/2021 | Chui |
| 2021/0113167 A1 | 4/2021 | Chui |
| 2021/0118199 A1 | 4/2021 | Chui |
| 2022/0005277 A1 | 1/2022 | Chen |
| 2022/0013089 A1 | 1/2022 | Kreeger |
| 2022/0192615 A1 | 6/2022 | Chui |
| 2023/0053489 A1 | 2/2023 | Kreeger |
| 2023/0054121 A1 | 2/2023 | Chui |

FOREIGN PATENT DOCUMENTS

| | | |
|---|---|---|
| CN | 202161328 | 3/2012 |
| CN | 102429678 | 5/2012 |
| CN | 107440730 | 12/2017 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 3060132 | 4/2019 |
| JP | H09-198490 | 7/1997 |
| JP | H09-238934 | 9/1997 |
| JP | H10-33523 | 2/1998 |
| JP | 2000-200340 | 7/2000 |
| JP | 2002-282248 | 10/2002 |
| JP | 2003-189179 | 7/2003 |
| JP | 2003-199737 | 7/2003 |
| JP | 2003-531516 | 10/2003 |
| JP | 2004254742 | 9/2004 |
| JP | 2006-519634 | 8/2006 |
| JP | 2006-312026 | 11/2006 |
| JP | 2007-130487 | 5/2007 |
| JP | 2007-330334 | 12/2007 |
| JP | 2007-536968 | 12/2007 |
| JP | 2008-068032 | 3/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012/501750 | 1/2012 |
| JP | 2012011255 | 1/2012 |
| JP | 2012-061196 | 3/2012 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 2005051197 | 6/2005 |
| WO | 2005/110230 | 11/2005 |
| WO | 2005110230 | 11/2005 |
| WO | 2005/112767 | 12/2005 |
| WO | 2005112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008/014670 | 2/2008 |
| WO | 2008047270 | 4/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |
| WO | 2016/103094 | 6/2016 |
| WO | 2016/184746 | 11/2016 |
| WO | 2018/183548 | 10/2018 |
| WO | 2018/183549 | 10/2018 |
| WO | 2018/183550 | 10/2018 |
| WO | 2018/236565 | 12/2018 |

OTHER PUBLICATIONS

Dromain, Clarisse et al., "Dual-energy contrast-enhanced digital mammography: initial clinical results", European Radiology, Sep. 14, 2010, vol. 21, pp. 565-574.

Reynolds, April, "Stereotactic Breast Biopsy: A Review", Radiologic Technology, vol. 80, No. 5, Jun. 1, 2009, pp. 447M-464M, XP055790574.

"Filtered Back Projection", (NYGREN), published May 8, 2007, URL: http://web.archive.org/web/19991010131715/http://www.owlnet.rice.edu/~elec539/Projects97/cult/node2.html, 2 pgs.

Berg WA et al., "Combined screening with ultrasound and mammography vs mammography alone in women at elevated risk of breast cancer", JAMA 299:2151-2163, 2008.

Canadian Office Action in Application 2829349, dated Oct. 15, 2018, 4 pages.

Carton AK, et al., "Dual-energy contrast-enhanced digital breast tomosynthesis—a feasibility study", BR J Radiol. Apr. 2010;83 (988):344-50.

Chen SC, et al., "Initial clinical experience with contrast-enhanced digital breast tomosynthesis", Acad Radio. Feb. 2007 14(2):229-38.

Chinese 2nd Office Action in Application 201480058064.5, dated Jul. 16, 2019, 5 pgs.

(56) References Cited

OTHER PUBLICATIONS

Diekmann F., et al., "Digital mammography using iodine-based contrast media: initial clinical experience with dynamic contrast medium enhancement", Invest Radiol 2005; 40:397-404.
Dromain C., et al., "Contrast enhanced spectral mammography: a multi-reader study", RSNA 2010, 96th Scientific Assembly and Scientific Meeting.
Dromain C., et al., "Contrast-enhanced digital mammography", Eur J Radiol. 2009; 69:34-42.
EP Extended Search Report dated Jul. 18, 2014 in EP App 12754521.8, 7 pages.
European Communication in Application 10707751.3, dated Oct. 4, 2018, 5 pages. (corresponding to 0.0020USU1 matter).
European Communication in Application 10707751.3, dated Aug. 7, 2019, 6 pages.
European Extended Search Report for European Patent Application No. 14770362.3 dated Sep. 28, 2016, 8 pgs.
European Extended Search Report in Application 14855181.5, dated May 15, 2017, 7 pages.
European extended Search Report in Application 18153706.9, dated Jun. 1, 2018, 8 pages.
European Mar. 23, 2009 European Search Report in connection with counterpart European patent Application No. 07750818.
European Office Action in Application 10707751.3, dated Feb. 19, 2018, 5 pgs.
Freiherr G., "Breast tomosynthesis trials show promise", Diagnostic Imaging—San Francisco 2005, V27; N4:42-48.
Giger, M. et al., "An "Intelligent" Workstation for Computer-aided Diagnosis", RadioGraphics, (1993), 13(3): 647-656.
Giger, M. et al., "Development of a "smart" workstation for use in mammography", Proceedings of SPIE, (1991), 45: 101-103.
Hologic, "Lorad StereoLoc II" Operator's Manual 9-500-0261, Rev. 005, 2004, 78 pgs.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
ICRP Publication 60: 1990 Recommendations of the International Commission on Radiological Protection.
Japanese Notice of Final Rejection in Application 2016-526115, dated Jun. 24, 2019, 5 pages.
Jochelson M., et al, Bilateral, RSNA 2010, 96th Scientific Assembly and Scientific Meeting.
Jong, RA, et al., Contrast-enhanced digital mammography: initial clinical experience. Radiology 2003; 228:842-850.
Kopans, et.al. Will tomosynthesis replace conventional mammography? Plenary Session SFN08: RSNA 2005.
Lehman CD, et al. MRI evaluation of the contralateral breast in women with recently diagnosed breast cancer. N Engl J Med 2007; 356:1295-1303.
Lewin JM, et al., Dual-energy contrast-enhanced digital subtraction mammography: feasibility. Radiology 2003; 229:261-268.
Lindfors KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
Observations by Third Party, Remarks concerning European patent application No. 10707751.3 according to Article 115 EPC, dated Apr. 24, 2014, 8 pgs.
PCT Feb. 20, 2008 International Search Report and Written Opinion in connection with corresponding International patent application No. PCT/US2007/04006, 7 pgs.
PCT International Preliminary Report on Patentability in International Application PCT/US2014/061994, dated Apr. 26, 2016, 5 pages.
PCT International Search Report and Written Opinion in Application PCT/US2010/025873, dated Aug. 2, 2010, 19 pgs.

PCT International Search Report in Application PCT/US2014/026164, dated Jul. 28, 2014, 1 page.
PCT International Written Report for International Application PCT/US2014/026164, dated Jul. 28, 2014, 12 pgs.
PCT Written Opinion in International Application PCT/US2014/061994, dated Jan. 22, 2015, 4 pages.
PCT/US12/28334 International Search Report and Written Opinion, dated Jul. 5, 2012.
Poplack SP, et al, Digital breast tomosynthesis: initial experience in 98 women with abnormal digital screening mammography. AJR Am J Roentgenology Sep. 2007 189(3):616-23.
Prionas ND, et al., Contrast-enhanced dedicated breast CT: initial clinical experience. Radiology. Sep. 2010 256(3):714-723.
Rafferty E. et al. Assessing Radiologist Performance Using Combined Full-Field Digital Mammography and Breast Tomosynthesis Versus Full-Field Digital Mammography Alone: Results . . . presented at 2007 Radiological Society of North America meeting, Chicago IL.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., Full field breast tomosynthesis. Radiol Manage. Sep.-Oct. 2005; 27(5):25-31.
Weidner N, Semple JP, Welch WR, Folkman J. Tumor angiogenesis and metastasis: correlation in invasive breast carcinoma. New England Journal of Medicine 1991; 324:1-8.
Weidner N, The importance of tumor angiogenesis: the evidence continues to grow. Am J Clin Pathol. Nov. 2004 122(5):696-703.
European Communication of a Notice of Opposition in Application 10707751.3, dated Sep. 13, 2021, 23 pages.
Burbank, Fred, "Stereotactic Breast Biopsy: Its History, Its Present, and Its Future", published in 1996 at the Southeastern Surgical Congress, 24 pages. (Reference labeled D9 in 0020 Opposition).
Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages. (Reference labeled D10 in 0020 Opposition).
Fischer Imaging Corp, Mammotest Plus manual on minimally invasive breast biopsy system, 2002, 8 pages.
Fischer Imaging Corporation, Installation Manual, MammoTest Family of Breast Biopsy Systems, 86683G, 86684G, P-55957-IM, Issue 1, Revision 3, Jul. 2005, 98 pages.
Fischer Imaging Corporation, Operator Manual, MammoTest Family of Breast Biopsy Systems, 86683G, 86684G, P-55956-OM, Issue 1, Revision 6, Sep. 2005, 258 pages.
Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.
Samani, A. et al., "Biomechanical 3-D Finite Element Modeling of the Human Breast Using MRI Data", 2001, IEEE Transactions on Medical Imaging, vol. 20, No. 4, pp. 271-279.
Yin, H.M., et al., "Image Parser: a tool for finite element generation from three-dimensional medical images", BioMedical Engineering Online. 3:31, pp. 1-9, Oct. 1, 2004.
Sakic et al., "Mammogram synthesis using a 3D simulation. I. breast tissue model and image acquisition simulation" Medical Physics. 29, pp. 2131-2139 (2002).
Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).
Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).
Al Sallab et al., "Self Learning Machines Using Deep Networks", Soft Computing and Pattern Recognition (SoCPaR), 2011 Int'l. Conference of IEEE, Oct. 14, 2011, pp. 21-26.

(56) References Cited

OTHER PUBLICATIONS

Caroline, B.E. et al., "Computer aided detection of masses in digital breast tomosynthesis: A review", 2012 International Conference on Emerging Trends in Science, Engineering and Technology (INCOSET), Tiruchirappalli, 2012, pp. 186-191.
Ertas, M. et al., "2D versus 3D total variation minimization in digital breast tomosynthesis", 2015 IEEE International Conference on Imaging Systems and Techniques (IST), Macau, 2015, pp. 1-4.
Ghiassi, M. et al., "A Dynamic Architecture for Artificial Networks", Neurocomputing, vol. 63, Aug. 20, 2004, pp. 397-413.
Chan, Heang-Ping et al., "ROC Study of the effect of stereoscopic imaging on assessment of breast lesions," Medical Physics, vol. 32, No. 4, Apr. 2005, 1001-1009.
Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.
Pediconi, "Color-coded automated signal intensity-curve for detection and characterization of breast lesions: Preliminary evaluation of new software for MR-based breast imaging," International Congress Series 1281 (2005) 1081-1086.
EFilm Mobile HD by Merge Healthcare, web site: http://itunes.apple.com/bw/app/efilm-mobile-hd/id405261243?mt=8, accessed on Nov. 3, 2011 (2 pages).
EFilm Solutions, eFilm Workstation (tm) 3.4, website: http://estore.merge.com/na/estore/content.aspx?productID=405, accessed on Nov. 3, 2011 (2 pages).
Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.
E. Shaw de Paredes et al., "Interventional Breast Procedure", published Sep./Oct. 1998 in Curr Probl Diagn Radiol, pp. 138-184.
Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.
Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.
Conner, Peter, "Breast Response to Menopausal Hormone Therapy—Aspects on Proliferation, apoptosis and Mammographic Density", 2007 Annals of Medicine, 39;1, 28-41.
Glick, Stephen J., "Breast CT", Annual Rev. Biomed. Eng., 2007, 9;501-26.
Metheany, Kathrine G. et al., "Characterizing anatomical variability in breast CT images", Oct. 2008, Med. Phys. 35 (10); 4685-4694.
Dromain, Clarisse, et al., "Evaluation of tumor angiogenesis of breast carcinoma using contrast-enhanced digital mammography", AJR: 187, Nov. 2006, 16 pages.
Zhao, Bo, et al., "Imaging performance of an amorphous selenium digital mammography detector in a breast tomosynthesis system", May 2008, Med. Phys 35(5); 1978-1987.
Mahesh, Mahadevappa, "AAPM/RSNA Physics Tutorial for Residents—Digital Mammography: An Overview", Nov.-Dec. 2004, vol. 24, No. 6, 1747-1760.
Zhang, Yiheng et al., "A comparative study of limited-angle cone-beam reconstruction methods for breast tomosythesis", Med Phys., Oct. 2006, 33(10): 3781-3795.
Sechopoulos, et al., "Glandular radiation dose in tomosynthesis of the breast using tungsten targets", Journal of Applied Clinical Medical Physics, vol. 8, No. 4, Fall 2008, 161-171.
Wen, Junhai et al., "A study on truncated cone-beam sampling strategies for 3D mammography", 2004, IEEE, 3200-3204.
Ijaz, Umer Zeeshan, et al., "Mammography phantom studies using 3D electrical impedance tomography with numerical forward solver", Frontiers in the Convergence of Bioscience and Information Technologies 2007, 379-383.
Kao, Tzu-Jen et al., "Regional admittivity spectra with tomosynthesis images for breast cancer detection", Proc. Of the 29th Annual Int'l. Conf. of the IEEE EMBS, Aug. 23-26, 2007, 4142-4145.
Varjonen, Mari, "Three-Dimensional Digital Breast Tomosynthesis in the Early Diagnosis and Detection of Breast Cancer", IWDM 2006, LNCS 4046, 152-159.
Taghibakhsh, f. et al., "High dynamic range 2-TFT amplified pixel sensor architecture for digital mammography tomosynthesis", IET Circuits Devices Syst., 2007, 1(10, pp. 87-92.
Chan, Heang-Ping et al., "Computer-aided detection system for breast masses on digital tomosynthesis mammograms: Preliminary Experience", Radiology, Dec. 2005, 1075-1080.
"Supersonic to feature Aixplorer Ultimate at ECR", AuntiMinnie.com, 3 pages (Feb. 2018).
Kopans, Daniel B., "Breast Imaging", 3rd Edition, Lippincott Williams and Wilkins, published Nov. 2, 2006, pp. 960-967.
Williams, Mark B. et al., "Optimization of exposure parameters in full field digital mammography", Medical Physics 35, 2414 (May 20, 2008); doi: 10.1118/1.2912177, pp. 2414-2423.
Elbakri, Idris A. et al., "Automatic exposure control for a slot scannong full field digital mammagraphy system", Med. Phys. Sep. 2005; 32(9):2763-2770, Abstract only.
Feng, Steve Si Jia, et al., "Clinical digital breast tomosynthesis system: Dosimetric Characterization", Radiology, Apr. 2012, 263(1); pp. 35-42.
European Transmittal of Decision and Summons to attend oral proceedings in EP Application 10707751.3, dated Mar. 8, 2022, 15 pages.

* cited by examiner

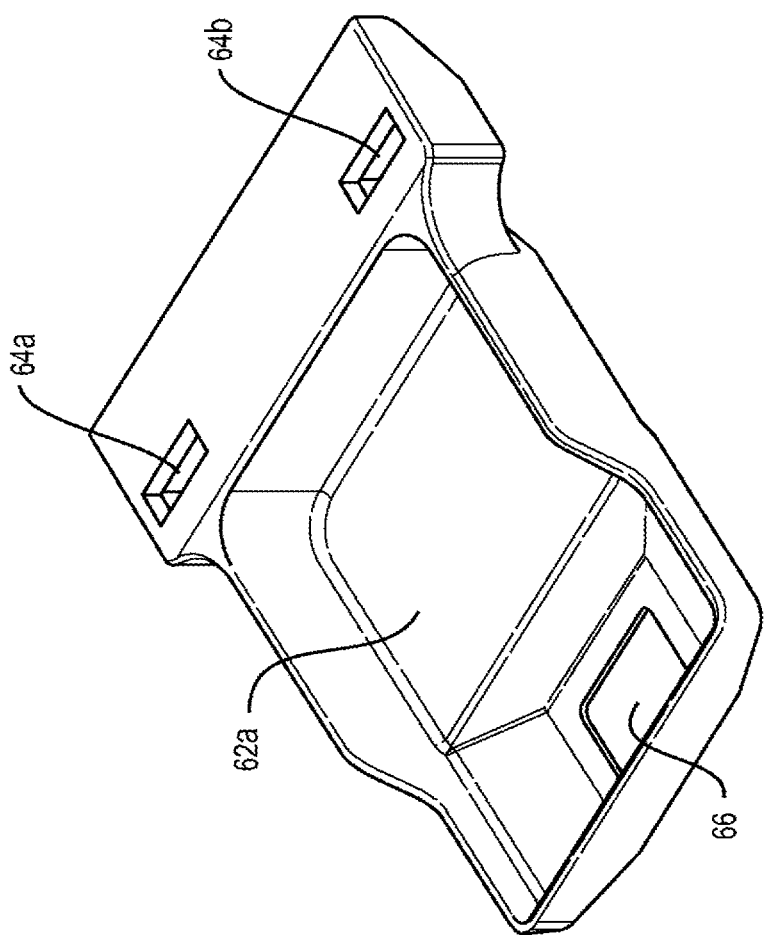

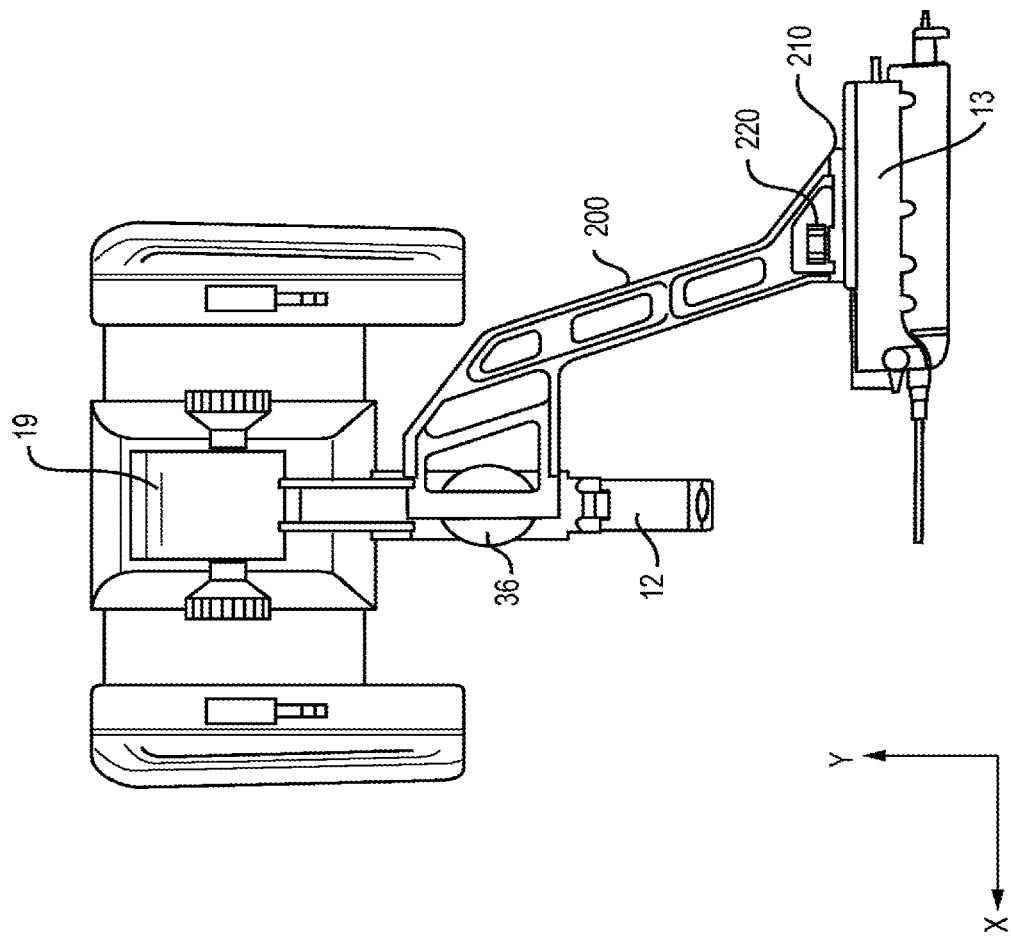

NEEDLE BREAST BIOPSY SYSTEM AND METHOD OF USE

RELATED APPLICATIONS

This application is a continuation of U.S. patent application Ser. No. 12/715,591, now U.S. Pat. No. 10,595,954, filed Mar. 2, 2010; which claims priority pursuant to 35 U.S.C. § 1.119(e) to provisional patent application Ser. No. 61/249,772 filed Oct. 8, 2009, the disclosures of which are hereby incorporated herein by reference in their entireties.

BACKGROUND OF THE INVENTION

Mammography is a well-established method of breast imaging which may be used for breast cancer screening and diagnosis. Screening mammograms are preferably obtained annually for female members of the population over the age of forty, or those having a genetic risk of breast cancer. Should masses or calcifications ('regions of interest') be identified during a screening mammogram, the patient may require further diagnosis. Such diagnosis may involve biopsying the region of interest and analyzing excised tissue.

Various imaging modalities have historically been used during breast biopsies. The imaging modalities include ultrasound imaging, x-ray imaging and magnetic resonance imaging. Performing a breast biopsy typically involves positioning the patient, visualizing the region of interest using the imaging equipment, targeting coordinates of the region and retrieving cells or tissue from the targeted region. Cells or tissue may be retrieved in a variety of ways, including through open surgery, fine needle aspiration, core needle biopsy or vacuum assisted biopsy. Open surgery, the most invasive procedure, is generally performed by a radiologist placing a wire into the breast during visualization of the region of interest, where the wire extends into the region that is to be excised. The patient is then transferred to surgery and tissue is retrieved using the wire to locate the region of interest.

Fine needle aspiration, core needle biopsies and vacuum assisted biopsies are less invasive than open surgery, allowing cells and tissue to be obtained without the need for open surgery. All are needle biopsies, with the size of the needle, and thus the corresponding size (and number) of the biopsied samples, being differentiators. In each procedure the patient is positioned, the region of interest is visualized, the needle of the biopsy device is advanced to the target region of interest and the tissue is retrieved. Fine needle aspiration and core needle biopsy devices typically retrieve one tissue sample and their advancement to the target may be monitored using an imaging modality such as ultrasound. Vacuum assisted biopsy devices generally have larger needles and can extract multiple cores.

X-ray imaging in stereotactic mode is generally used for breast biopsies because it is desirable to visualize and target regions in a three dimensional volume. Stereotactic biopsies obtain volume information using x-ray images taken in at least two planes. The x-ray images are then processed to localize a target region of interest in three-dimensional space using the principal of parallax to determine the depth, or Z dimension, of the target region.

U.S. Patent Application 2008/0045833, filed Feb. 21, 2008 and incorporated herein by reference, describes systems and methods for using tomosynthesis for lesion localization during breast biopsy. Tomosynthesis (tomo) is a method of performing three dimensional (3D) breast x-ray imaging. It generates images of cross sectional slices through a compressed breast, and also is used to identify breast pathologies. One of the advantages of tomosynthesis is that the images are three-dimensional so that once an area of interest is identified in an image its exact 3D coordinate in the breast can be calculated or estimated, e.g. from the x, y coordinate in the image of a slice and from the z, or depth, coordinate given by the image slice depth location. Another advantage of tomosynthesis is its ability to provide high contrast visibility of objects by the suppression of images from objects at different heights in the breast. Because of its superior contrast visibility, it is expected that there will be pathologies seen on the tomo images that will not be visible using standard x-ray mammography, stereotactic devices, ultrasound or even MRI. For this reason, it is desired to develop localization methods using tomosynthesis systems that utilize tomosynthesis' natural 3D localization abilities.

SUMMARY OF THE INVENTION

According to one aspect of the invention a stereotactic needle biopsy assembly is provided for mounting between an x-ray source and a detector of an x-ray imaging system. The stereotactic assembly includes a mounting arm for supporting a biopsy device at an angle offset from normal to a plane of defined by the detector. In some embodiments, the assembly may also include a lateral side arm permitting lateral access to the breast. The stereotactic needle biopsy assembly includes a guidance module for motorized guidance of the biopsy device to a target location during a biopsy for excising tissue. Because the biopsy needle is angled relative to the detector, x-ray imaging may be performed during the biopsy procedure without interference by the biopsy device. In addition the angled biopsy needle allows improved access to the axilla and chest wall of the patient.

In one embodiment the needle biopsy assembly includes a motor or equivalent mechanism enabling automatic advancement of the biopsy device towards an identified biopsy target location. The system advantageously additionally includes mechanisms enabling manual advancement of the device. The system permits the user to define stop locations along the biopsy path to the target, for transitioning between automated and manual control.

In one embodiment the needle biopsy assembly may include a control module, mounted on the needle biopsy assembly, the control module enabling the medical personnel to control the automated movement of the device towards the target without leaving the patient. The control module in some embodiments may display information related to the biopsy procedure, such as the relative locations of the needle and the target. The control module may also provide visible or audible warnings to the user, for example to warn of proximity of the needle to the chest wall, the breast platform, or other undesirable position. In one embodiment the control buttons of the control module are arranged to preclude unintended advancement of the biopsy device.

The stereotactic biopsy device of the present invention may be coupled to any x-ray system, whether upright or prone, including but not limited to mammography systems, tomosynthesis systems, and combination mammography/tomosynthesis systems. The system flexibly supports the use of any mode of image capture (i.e., scout, two dimensional mammogram, three-dimensional reconstructed volume) and any combination of two dimensional or three dimensional image data for either or both target visualization and target localization. With such an arrangement, a needle biopsy assembly having improved patient coverage is provided for use with a variety of different x-ray imaging platforms.

In particular such an assembly may easily be integrated into a tomosynthesis imaging system. Such a tomosynthesis system could be readily adapted to provide automated stereotactic image capture for use with the needle biopsy assembly by capturing tomo projection images at desired stereotactic angles. Such a system has the added advantage of reducing patient exposure because tomosynthesis projection images are generally obtained at lower dose than conventional mammograms and therefore stereotactic volume information (for use in visualization or targeting) can be obtained at reduced dosage. These and other advantages will be described in further detail below.

BRIEF DESCRIPTION OF THE FIGURES

FIGS. 6A-6C illustrate compression paddles which may advantageously be used with the needle biopsy assembly of FIG. 2;

FIGS. 12A-12C illustrate views of an embodiment of the needle biopsy assembly with a lateral biopsy arm attachment.

DETAILED DESCRIPTION

Figure 1:
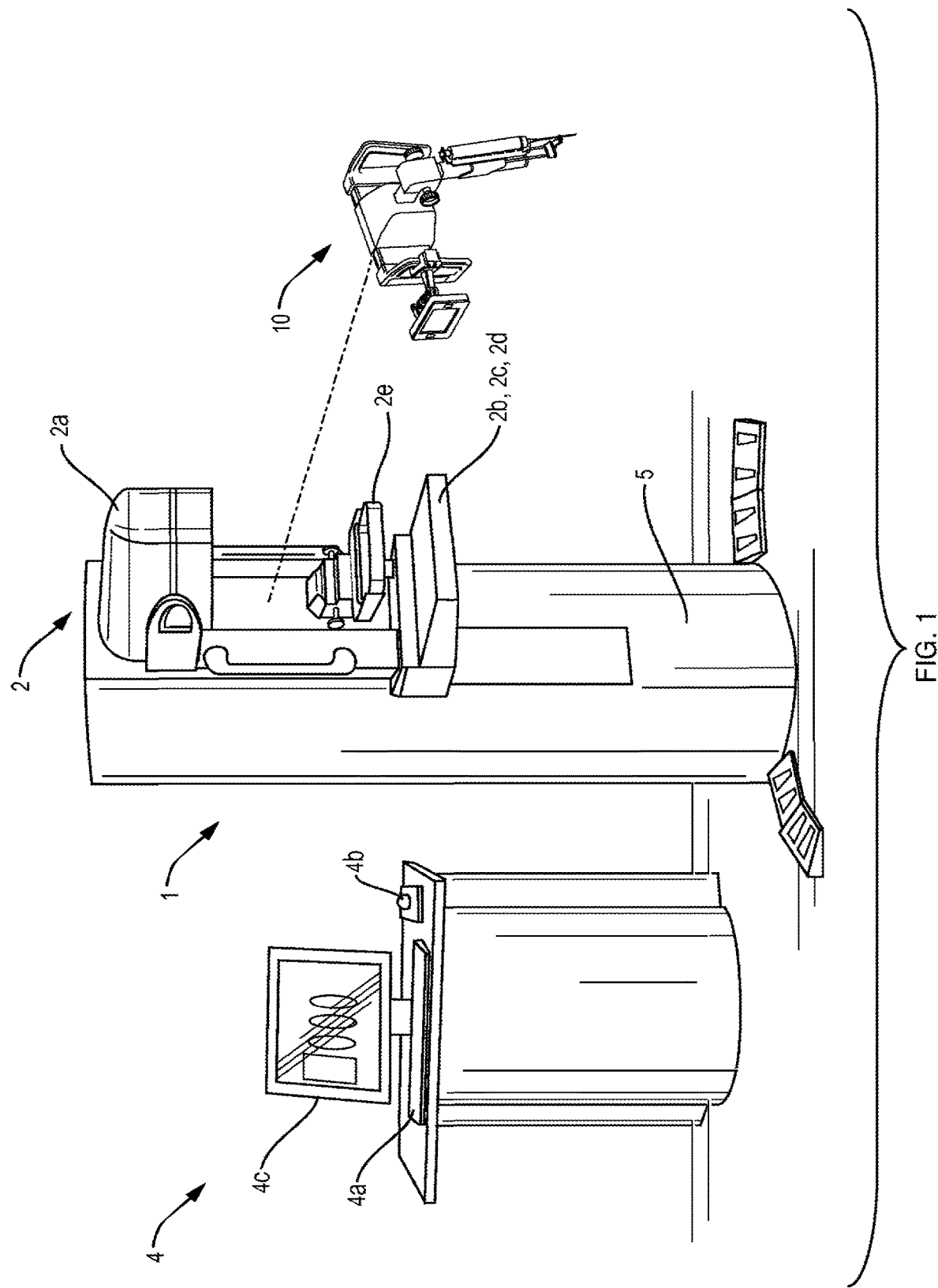
FIG. 1 illustrates an x-ray imaging system which may advantageously incorporate the needle biopsy assembly of the present invention.

Breast tomosynthesis systems generally include an x-ray source mounted on a rotatable arm of a gantry and an x-ray detector positioned generally normal to the x-ray source when the x-ray source is at zero position. During tomosynthesis image acquisition, the x-ray source is rotated over a limited angular range. At various points in the x-ray source trajectory the source is activated and an image is captured by the detector. Each image captured at each point is referred to as a projection image. Computer programs are used to reconstruct a three dimensional volume from the projection images and the three dimensional volume is used for lesion detection. One example of an x-ray imaging system capable of mammographic and tomosynthesis imaging and which may be adapted to incorporate the present invention is shown in FIG. 1.

The mammography/tomosynthesis system is shown to include an acquisition work station (AWS) 4 and gantry 1 supporting an x-ray imaging assembly 2. Such a mammography/tomosynthesis system is currently available from the common assignee under the trade name Selenia Dimensions, and is representative of merely one x-ray system on which the needle biopsy assembly 10 of the present invention may be mounted. The gantry 1 supports a C-arm that can move up or down along the gantry to a selected height, driven by motor(s) controlled by a health professional operating the system. C-arm carries an x-ray tube 2a at an upper end and a breast tray 2b at a lower end. Tray 2b covers a flat panel x-ray image receptor 2c, spaced from the tray by a focused anti-scatter grid 2d (which may be retractable so that it can be removed from the space between tray 2b and receptor 2c). The C-arm also carries a compression paddle 2e that is between source 2a and breast tray 2b and is motorized to move away from tray 2b so a patient's breast can fit between tray 2b and paddle 2e, and closer to tray 2b so the patient's breast can be compressed and immobilized. The movement of paddle 2e is motorized and controlled by the health professional. Paddles 2e of different size and different configurations can be fitted on the gantry to suit different breast sizes or to suit imaging needs (i.e., for screening or diagnosis). In addition, the health professional can move paddle 2e along the width of tray 2b to a position in which paddle 2e matches the position of a breast that is not centered on tray 2b, as in the Selenia system currently offered by the common assignee. The system further includes other components, such as a control station 4 comprising interface devices such a keyboard 4a and trackball 4b, a display screen 4c, and control and image processing facilities.

According to one aspect of the invention a needle biopsy assembly 10 may easily be mounted in between the x-ray source and the x-ray detector of the imaging system 2. Unlike previous needle biopsy assemblies, the needle biopsy assembly of the present invention utilizes all of the existing components of the x-ray system, including the compression device and the x-ray detector. As a result, it can be appreciated that the needle biopsy assembly is a low cost solution which makes upright needle biopsy capability available to a variety of current x-ray imaging platforms.

Figure 2:
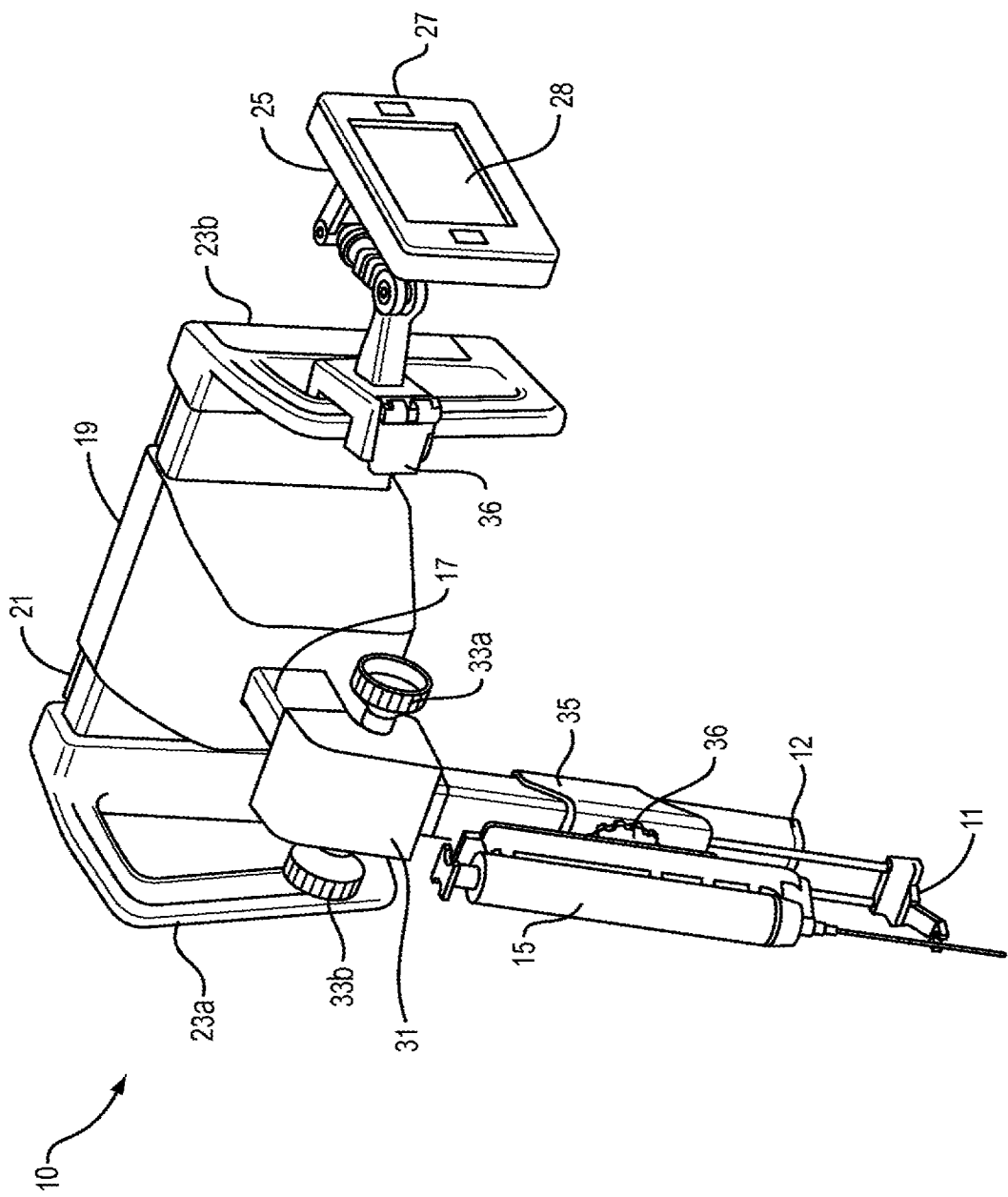
FIG. 2 illustrates one embodiment of the needle biopsy assembly of the present invention with a mounted biopsy device.

FIG. 2 illustrates the needle biopsy assembly 10 in more detail. Support bracket 21 extends between handles 23a and 23b, which facilitate transport of the assembly. Guidance module 19, mounted on support bracket 21, includes components for controlling the movement of the biopsy device 15. The biopsy device may be, for example, an Eviva™ vacuum assisted biopsy device manufactured and sold by Hologic, Inc. Fixed support arm 17 extends from the guidance module to connector 31. In one embodiment connector 31 connects angular support arm 12 to the fixed support arm 17 at a fixed angle. Alternative embodiments which include adjustment mechanisms for varying the angle of displacement between the angular support arm and the fixed support arm may be substituted herein as equivalents. Holster mount 35 is moveably coupled to the support arm. The linear movement may be mechanically controlled (i.e., via the guidance module and associated motors) and/or may be manually controlled using either or both of the thumbwheel knobs 33a and 33b. The holster mount 35 includes an attachment mechanism 36 that is adapted to receive biopsy holster 13. The biopsy device 15 sits within the biopsy holster 13. A needle support 11 may advantageously be coupled to the holster mount for needle stabilization. A control module 25 may be mounted to either of the handles, 23b or 23a via clamp 36. In various embodiments, each handle may include one or more electrical connectors which enable communication between the clamped control module 25 and the guidance module 19, and the medical professional may move the control module to either handle as a matter of preference. The control module 25 includes a user interface that enables a medical professional to control the biopsy procedure without the need to leave the patient. The control module includes a display 28 for displaying a status or other information about the biopsy, and one or more buttons 27 for controlling the movement of the biopsy device during the procedure.

Figure 3A:
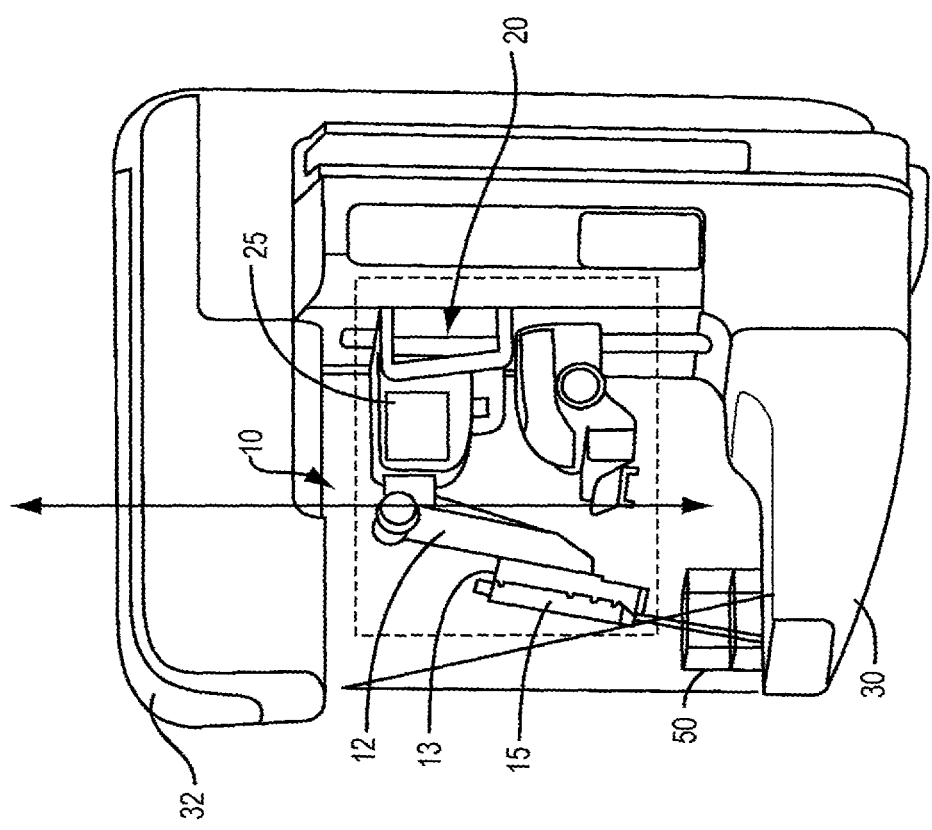
FIGS. 3A and 3B illustrates a portion of an x-ray system on which the needle biopsy assembly of the present invention is mounted and is used to illustrate how the angular tilt of the biopsy device reduces interference during x-ray imaging.
Figure 3B:
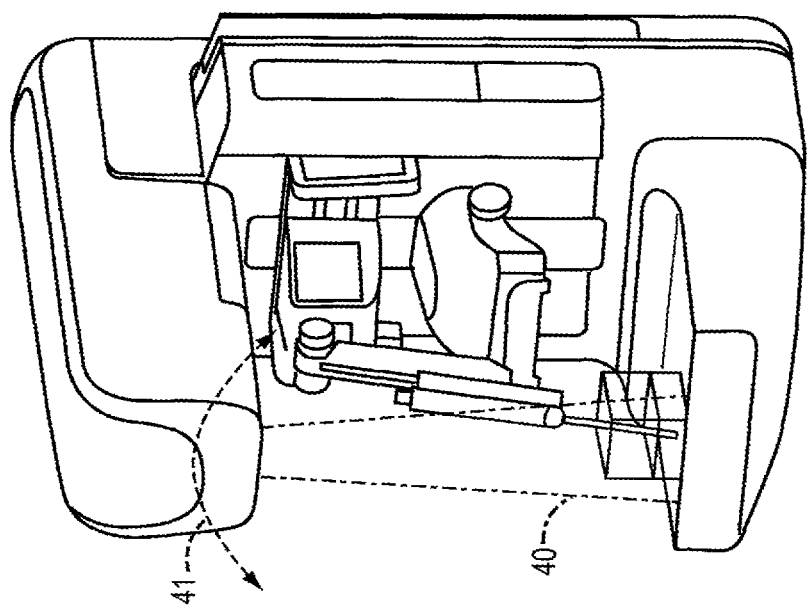

FIGS. 3A and 3B illustrate the needle biopsy assembly 10 mounted on a gantry of an x-ray imaging system. Various embodiments of the needle biopsy assembly may be used with either an upright or prone imaging system, for the purposes of this application an embodiment for use with an upright breast tomosynthesis imaging system (such as the Dimensions™ Breast Tomosynthesis imaging system provided by Hologic, Inc.) is described. An exemplary tomosynthesis imaging system may include a tube head 32 supporting a cone beam or other x-ray source, and a compression platform 30 encasing an x-ray detector. The tube head 32 is rotatably mounted on a gantry (not shown) to enable the tube head to rotate in along an angular trajectory generally designated by the dashed line 41 in FIG. 3B.

In one embodiment the needle biopsy assembly 10 includes clamps, hooks or other attachment means for mounting the needle biopsy assembly to the gantry of the tomosynthesis imaging system. Advantageously the clamps are mated to features of the gantry that support other attached devices (such as face shields and the like) although such reuse is not a requirement.

In the example of FIGS. 3A and 3B, the holster 13 is coupled to the holster mount on the a fixed angle arm 12, and the fixed angle arm 12 is fixedly mounted on the support arm 17 at an angle offset from normal by 10 degrees, although it is readily appreciated that the offset angle may vary and is largely a matter of design choice. Angling the arm 12 (and by consequence the biopsy device 15) allows the biopsy device to be advanced to a desired location within a biopsy target area (indicated generally by the target area 50) without the biopsy device and holster introducing artifacts into the x-ray image. As shown in FIG. 3B, the cone beam x-ray source will extend into the target area 50, but the device 15 does not fall within the cone beam. It should be noted that although a 10 degree fixed angle is disclosed, the present invention is not limited to any particular fixed angle and it is appreciated that the selected fixed angle may differ in response to particular geometries of the imaging systems and tissue removal tools. In a broadest sense, the present invention encompasses the idea of angling a biopsy needle to limit the introduction of visual artifacts caused by the needle during x-ray imaging.

Figure 4:
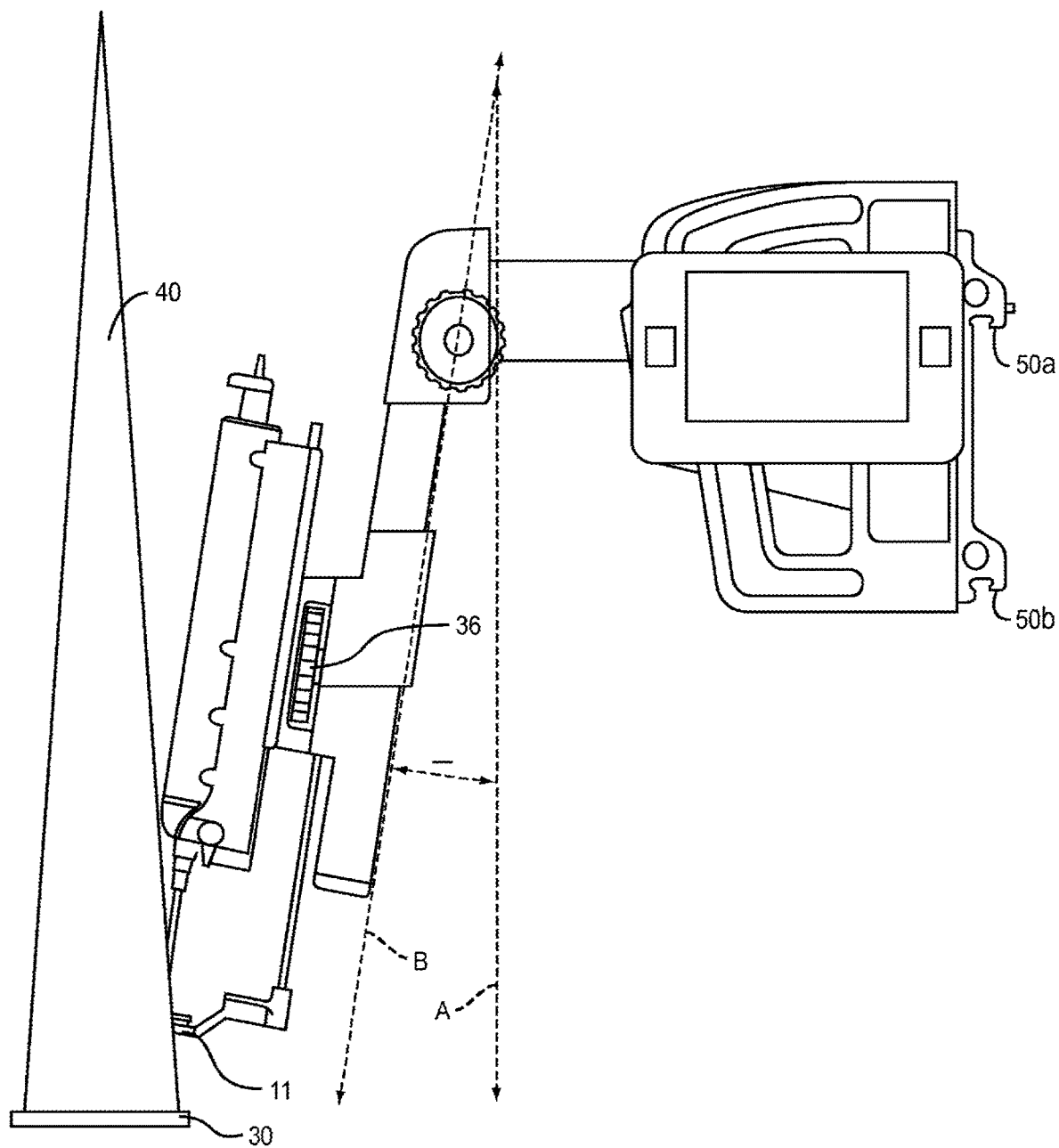
FIG. 4 is a side view of the needle biopsy assembly of the present invention, illustrating in more detail the angular tilt of the biopsy device support arm.

FIG. 4 is a side view of an exemplary embodiment of a needle biopsy assembly of the present invention. In FIG. 4, line A is within a plane that is 'normal' to the plane of the x-ray detector 30. Line B illustrates the angular displacement of the biopsy device, and therefore the device is offset from the normal by an angular measure of 0. As a result the biopsy device will interfere with biopsy imaging.

Also shown in more detail in FIG. 4 are exemplary coupling mechanisms 50a and 50b of the needle biopsy assembly 10. The coupling mechanisms 50a and 50b are adapted to mate with complementary features of the gantry. Other types of coupling mechanisms, including latches, hooks, slots and the like may be readily substituted herein as equivalents.

Figure 5:
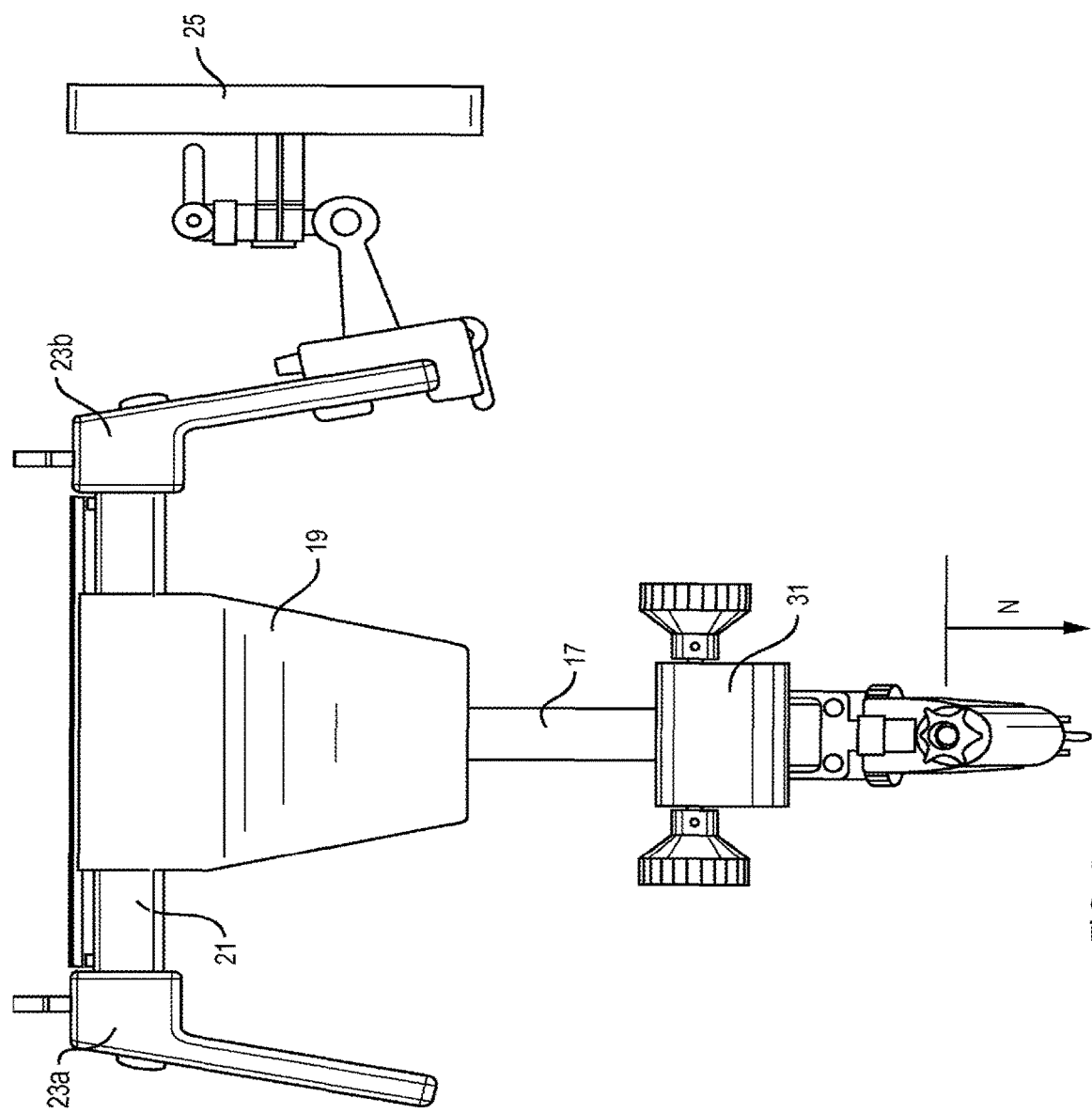
FIG. 5 is a top down view of the needle biopsy assembly of the present invention.

FIG. 5 is a top down view of the exemplary embodiment of the needle biopsy assembly, shown with only a subset of components labeled for ease of reference. When viewing the needle biopsy assembly from this perspective, the displacement N of the needle tip which results from the angular tilt of the biopsy device is readily apparent. This view best illustrates the ability of this device to biopsy areas of the breast (such as the axilla tissue and tissue near the chest wall) which were previously difficult to access using prior art stereotactic devices.

Figure 6C:
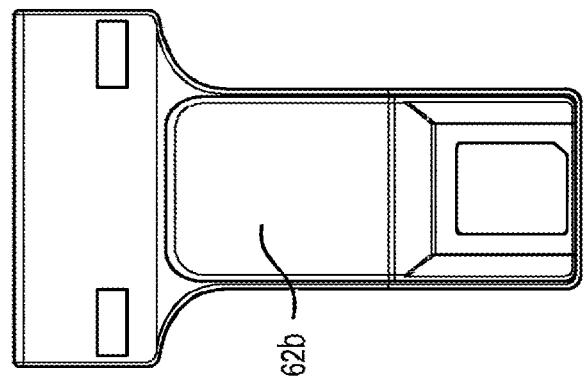
Figure 6B:
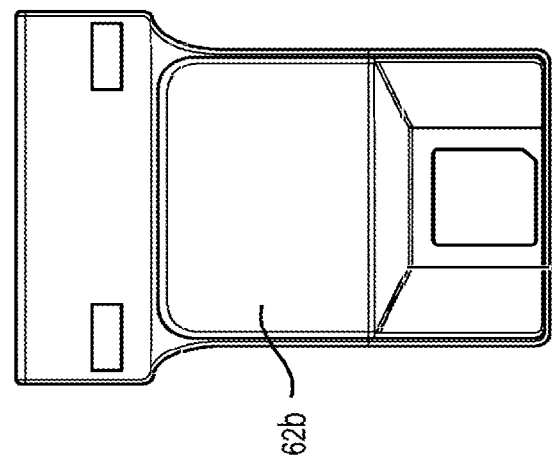
Figure 7:
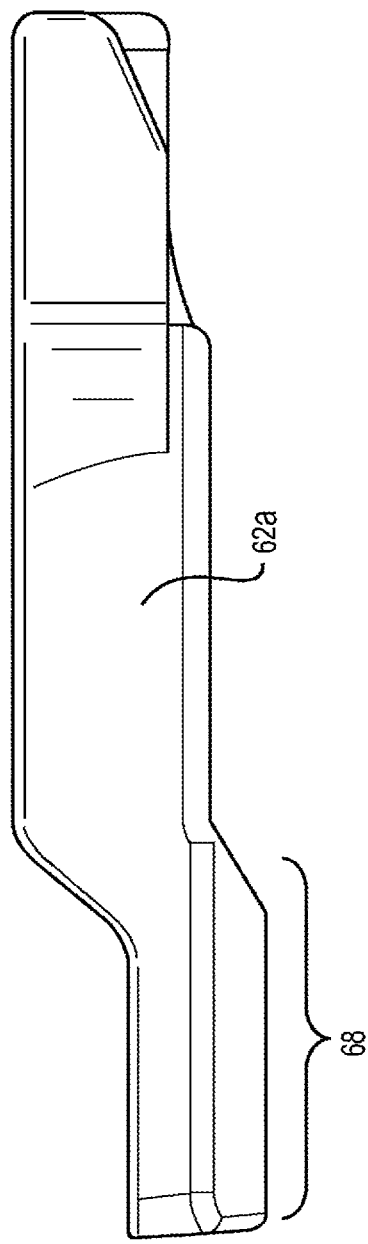
FIG. 7 is a side of a compression paddle which may be used with the needle biopsy assembly of the present invention.

FIGS. 6A through 6C illustrate various compression paddles which may be used with the present invention. In contrast to prior art needle biopsy compression paddles, which were generally fabricated of radio-opaque material having an opening therethrough for accepting the biopsy needle, the compression paddles 62A-62C are preferably radiolucent. Slots 64a and 64b are positioned to enable the compression paddle to be removably coupled to the compression device of the x-ray imaging system, allowing the paddles to easily be exchanged with the mammography/tomosynthesis paddles used for breast cancer screening. The biopsy compression paddles may be manufactured in different sizes to be used for different sized breasts, as shown in FIGS. 6B and 6C. An opening 66 is provided in each biopsy compression paddle. The opening enables the portion of the breast associated with the target to be exposed. As shown in FIG. 7, the portion 68 of the compression paddle 62a that surrounding the opening 66 is shaped to increase the compression on the portion of the breast being biopsied, thereby stabilizing the biopsied area.

One advantage of using the radiolucent breast compression paddle is that it allows full view of the detector; in prior art needle biopsy arrangement, only a portion of the detector associated with target localization was visible. This was sufficient because prior art biopsies were only performed on that portion of the tissue which was immediately below the opening in the compression paddle. However, the tilted needle of the present invention increases the amount of tissue that is available for biopsy beyond the border of the compression paddle opening—the needle in fact has the reach N shown in FIG. 5. Thus, as mentioned above, axilla tissue and tissue close to the chest wall can more readily be excised during biopsy.

Figure 8:
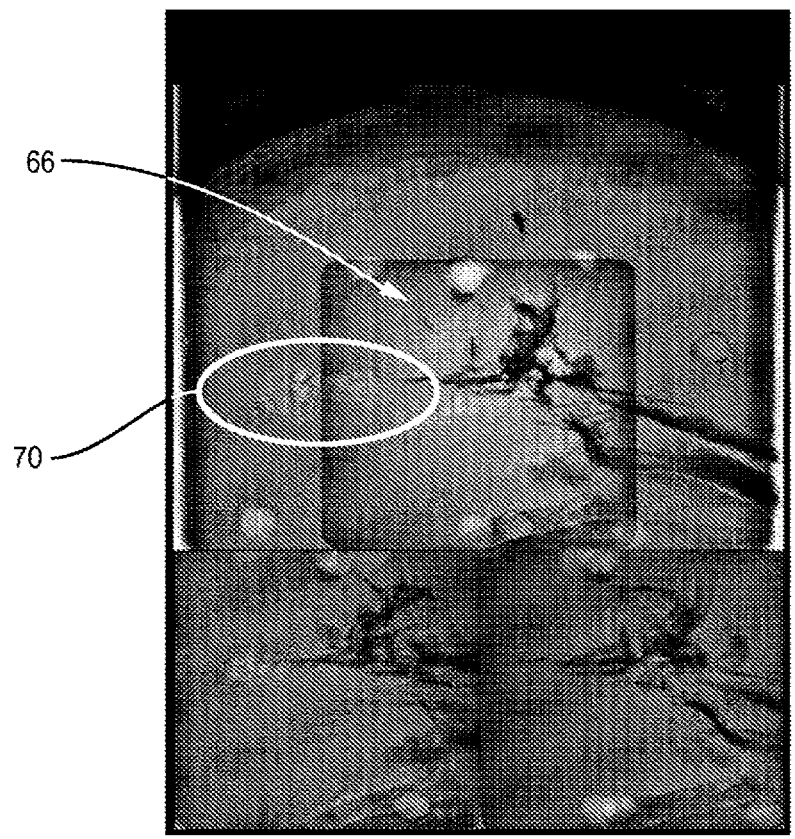
FIG. 8 illustrates an image capture at the acquisition workstation interface, wherein the entire detector is visible through the radiolucent compression paddle.

FIG. 8 illustrates a 2D image of a breast taken with a radiolucent biopsy paddle such as those shown in FIGS. 6 and 7. As shown in FIG. 8, one advantage of the radiolucent compression paddle is that the entire detector image may be viewed at the acquisition workstation interface; the radiologist is no longer limited in their access to information. As a result, the radiologist may see that portions of a lesion 80 extend beyond the compression paddle opening 66. This portion of the breast can be accessed using the tilted biopsy needle assembly of the present invention to ensure that all tissue is accessed for proper diagnosis.

Exemplary needle biopsy assemblies such as that described above may be generally used as follows. A patient who has been identified as a candidate for biopsy is positioned at the x-ray imaging system. At step 91 the biopsy compression paddle moves down towards the compression platform, compressing the patient's breast, and the process of visualizing the lesion is initiated at step 92. As mentioned briefly above, depending upon the capabilities of the x-ray imaging system, visualization of the lesion may be performed using a scout image, a mammogram, acquired stereotactic images, acquired tomosynthesis projection images, tomosynthesis reconstructed images, or any combination thereof. In one embodiment, an x-ray imaging system having tomosynthesis capabilities may be adapted to include a 'stereotactic mode', which, when selected, causes the x-ray imaging system to automatically retrieve the typical+/−15 degree stereotactic images and performs appropriate imaging processing on the stereotactic images to derive a stereotactic volume. One advantage of such an embodiment is that patient exposure may be reduced in tomosynthesis systems which use lower doses during projection image acquisition.

Once the lesion has been visualized, at step 93 the lesion is targeted. Targeting the lesion involves identifying the coordinates of the lesion using image data, and converting the coordinates from the Cartesian coordinate system of the images to the angular coordinate system of the tilted biopsy assembly using conversion techniques known to those of skill in the art. According to one aspect of the invention, different images, or combinations of images, may be used for visualizing the lesion than are used for targeting the lesion. For example, assume that a scout image is initially used to ensure that the patient is in position, and a pair of stereotactic images are used to visualize the lesion. If the lesion is found in the scout image, but not in both stereo images, the scout may be used in combination with the stereotactic image in which the lesion is located to derive target location information. Therefore, as above, depending upon the capabilities of the x-ray imaging system, the lesion target coordinates may be derived using a scout image, a mammogram, acquired stereotactic images, acquired tomosynthesis projection images, tomosynthesis reconstructed images, or any combination thereof.

Figure 10:
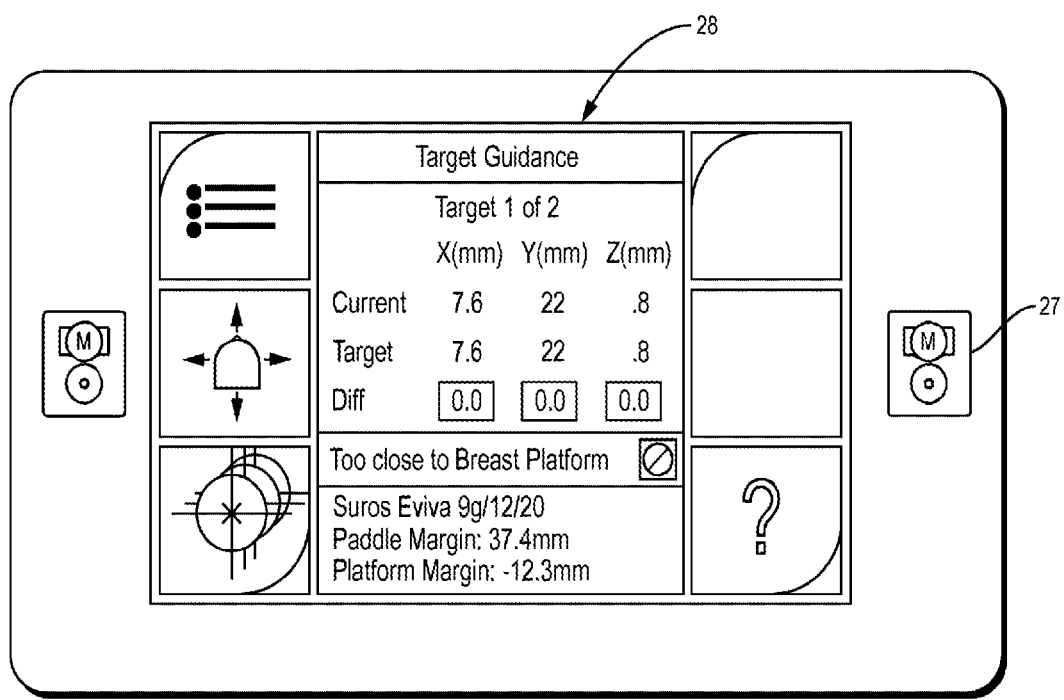
FIG. 10 illustrates an exemplary view of a user interface of the control unit of the needle biopsy assembly of FIG. 2.

At step 94, once the target coordinates are derived the medical professional can being the biopsy procedure by pressing control buttons required to move the biopsy needle. FIG. 10 illustrates an exemplary display and buttons of a control unit 25. The control unit includes a display 28 for displaying information related to the biopsy, such as information regarding needle size, distance to platform and paddle, needle coordinates, target coordinates, proximity to target and other related information. The control panel may also provide other helpful information to the user, such as warning indicators when the needle is too close to the breast platform, chest wall or skin line. As mentioned above, the warning indicators may be color coded or may provide other visual or audible indicators of undesirable conditions.

As mentioned above, in one embodiment the control unit also includes buttons (including button 27) positioned and arranged to allow single handed activation of the biopsy assembly while precluding accidental activation. In one embodiment, a pair of control buttons is provided, one on the front face of the control panel, and another on the back face of the control panel. Biopsy assembly movement may only be activated via simultaneous depression of both buttons. Other mechanisms for affirming operator intent may be substituted herein without affecting the scope of the invention.

According to one aspect of the invention, mechanical stops may be introduced into the biopsy path to stop automated needle movement at particular points along the path. For example, it may be desirable to switch to manual control of the needle movement, i.e, via knob 33a or 33b when the needle is within a desired range of the target. Or it may be desirable to provide a release brake for slow insertion of the needle into the breast. According to one embodiment, the number and location of mechanical stops is a programmable function which may be tailored to the individual preferences of a user of the system. Suffice it to say that numerous methods for mechanical advancement of the needle, including geared advancements, piston advancements, etc. are envisioned.

Figure 9:
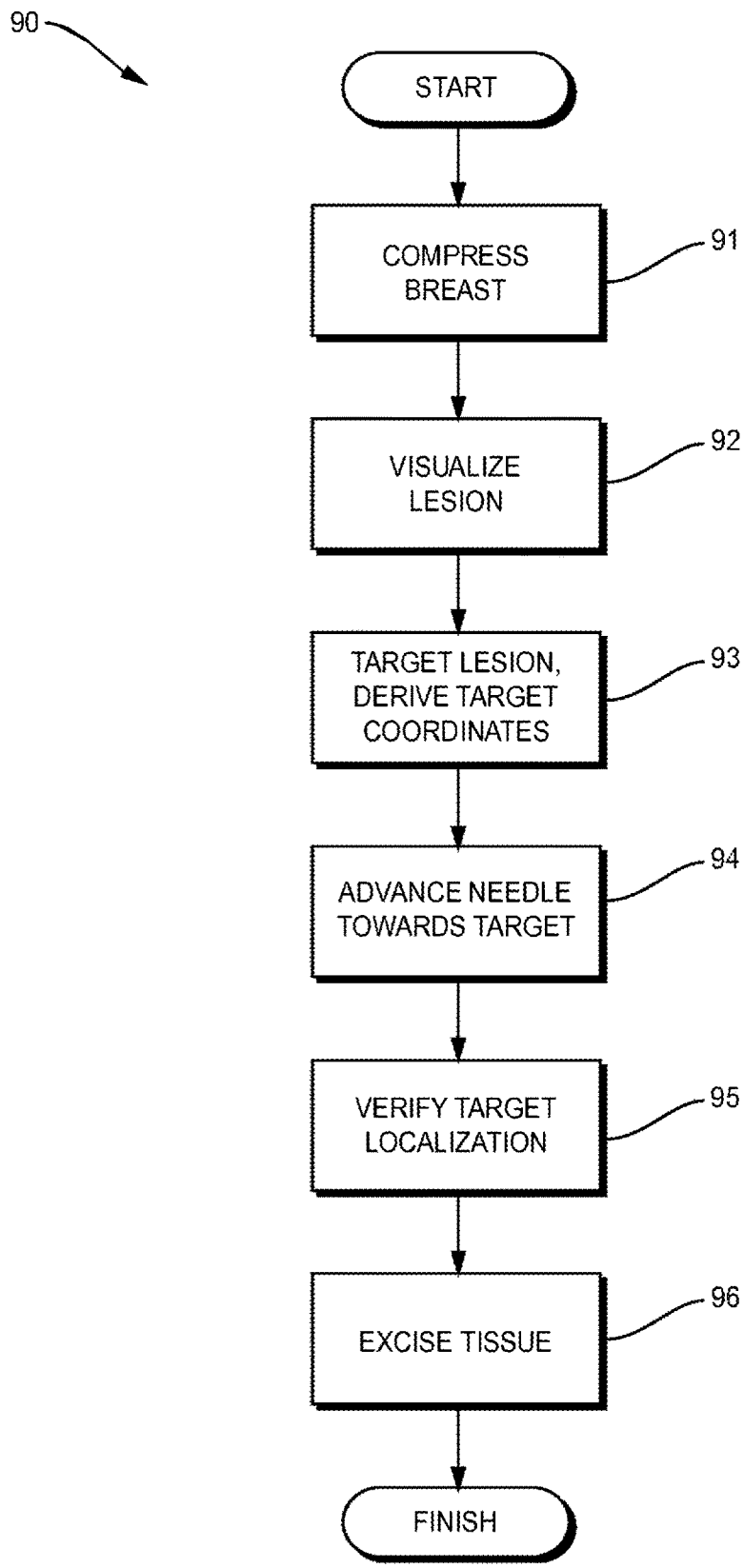
FIG. 9 is a flow diagram illustrating exemplary steps that may be performed during a biopsy using the needle biopsy assembly of the present invention.

Returning now to FIG. 9, at step 95 once the needle has been advanced to the target coordinates, an image may be acquired to verify that, in fact, the needle is positioned at the lesion. As the biopsy needle is out of the view of the x-ray imaging system such image may be obtained without interference. At step 96, when it is verified that the needle is at the target, the tissue may be excised, and the biopsy is complete. Although not explicitly shown in the flow diagram, steps 95 and 96 may be repeated to verify excision of the entire lesion.

Figure 11:
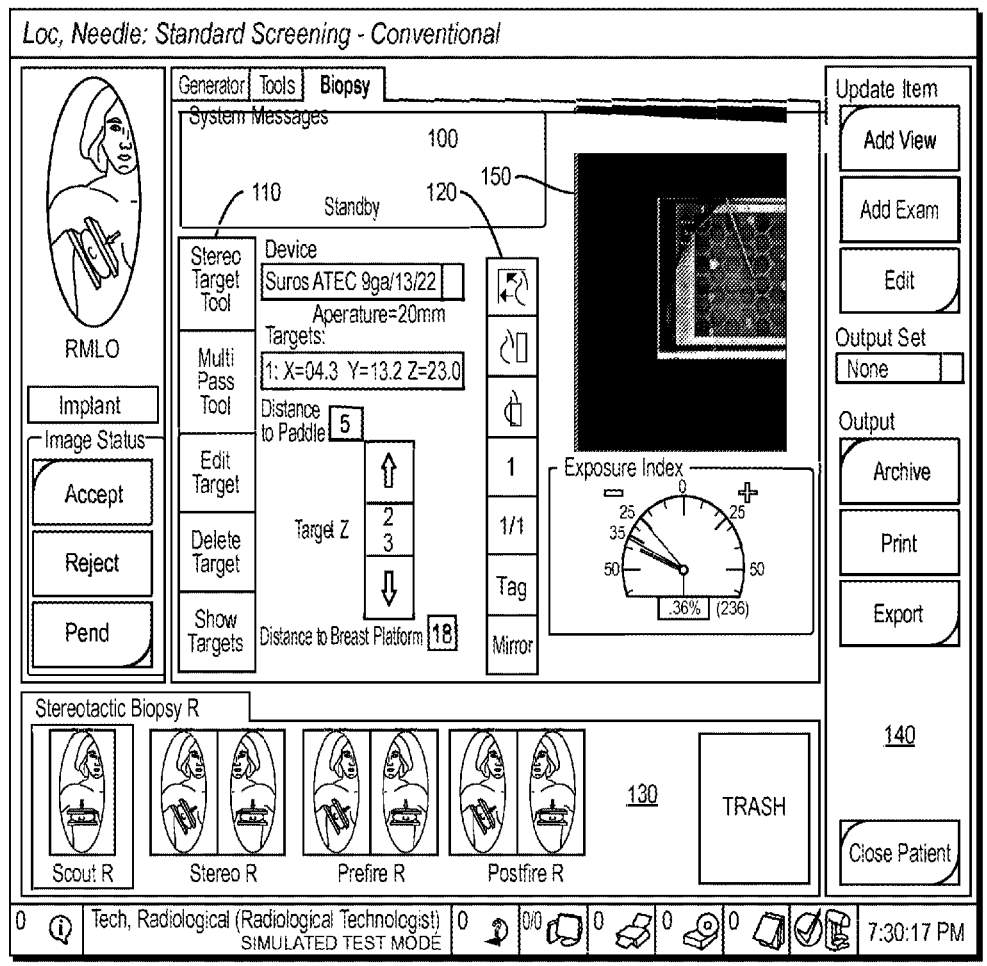
FIG. 11 illustrates an exemplary view of a user interface of an acquisition work station including functional modules and displays supporting and related to the needle biopsy assembly of FIG. 2.

Accordingly a biopsy needle assembly has been shown and described. According to another aspect of the invention, a user interface of the acquisition workstation is advantageously augmented with needle biopsy control capabilities, An example of user interface features that may be added to an acquisition workstation for use with the needle biopsy assembly is shown in FIG. 11. The user interface includes menus and/or control buttons or icons which enable the radiologist to control the display and output of information gathered during the biopsy. Targeting tools 110 allow the user to review, modify and delete target information. Image source selectors 120 (including stereotactic, tomosynthesis, scout, mammography, etc.) allow the radiologist to select which images to use for visualization or targeting. Image view selectors 130 allow the radiologist to quickly pull up and view any of the images that may have been acquired during the biopsy. Any of the images may be pulled up in the image window 150. Other information related to the biopsy, such as the type of biopsy device, the relative distances between the target and the compression plate/platform, etc., may also be included on the acquisition workstation. It should be noted that although a particular arrangement of buttons and icons has been shown in the representative view of FIG. 11, the present invention is not limited to any particular representation of such information, and other forms of pull down menus, hyperlinks, icons, buttons, and windows are considered equivalents hereto.

Figure 12C:
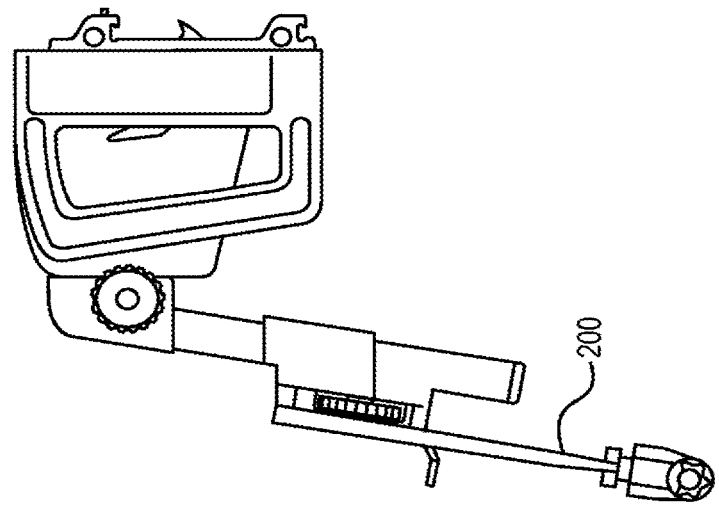
Figure 12B:
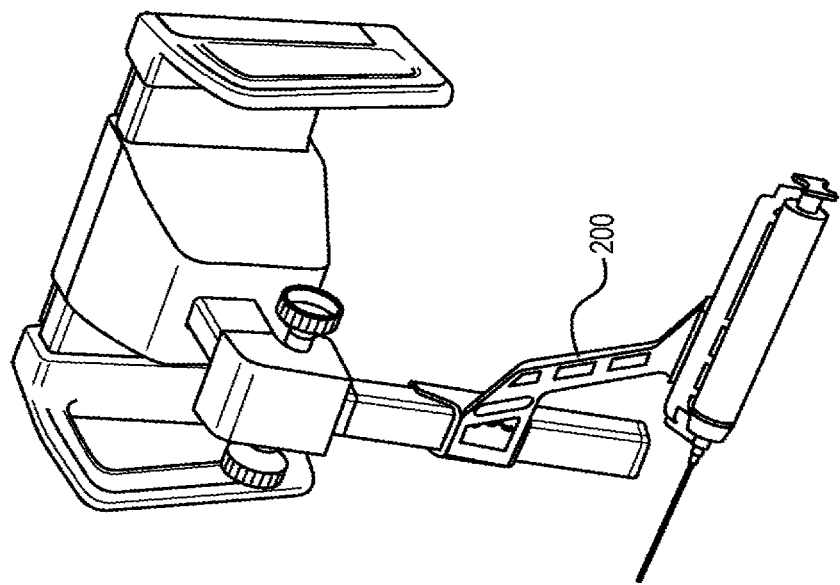

Although the above embodiments have described and illustrated a needle biopsy assembly for obtaining cores when the needle is positioned in a general cranial caudal orientation over the breast, according to one aspect of the invention lateral access to the breast may be achieved through the attachment of a lateral biopsy arm. The ability to perform lateral biopsies is particularly important for patients with thin breasts, as compression may reduce the thickness of the breast to such a degree that the tissue excision port at the distal tip of the biopsy needle cannot be fully inserted into the tissue. FIGS. 12A-12C illustrate various views of an embodiment of the needle biopsy assembly of the present invention that has been augmented with a lateral biopsy arm 200. FIG. 12A is a straight on view of the augmented assembly, FIG. 12B is a perspective view of the augmented assembly while FIG. 12C is a side view of the augmented assembly. The lateral biopsy arm supports the biopsy needle along a line substantially parallel to the detector, thereby permitting lateral excision of breast tissue. In the embodiment of FIGS. 12A-12C, the lateral biopsy arm includes a holster mount plate 210 and a thumb wheel 220. Rotation of the thumb wheel 220 results in manual translation of the needle in the direction indicated generally as X in FIG. 12A. Although manual translation in the X plane is shown, it is appreciated that motorized translation may be achieved by extending control from the guidance module 19 to the holster plate 210.

Targeting of the lesion, which defines how far the needle should move in the X,Y and Z direction is always done assuming that the needle is in a cranial—caudal orientation. According to one aspect of the invention, an electrical connection on the holster mount mounts with a connector on the lateral biopsy arm when the lateral biopsy arm is coupled to the holster mount 13 to enable the guidance module 19 to adjust the guidance coordinate system as appropriate for proper lesion localization.

Accordingly a tilted needle biopsy assembly having numerous advantages has been shown and described. Because the biopsy needle is angled relative to at least one of the detector and the x-ray source, x-ray imaging may be performed during the biopsy procedure without interference by the biopsy device. In addition the angled biopsy needle allows improved access to the axilla and chest wall of the patient. The stereotactic biopsy device of the present invention may be coupled to any x-ray system, whether upright or prone, including but not limited to mammography systems, tomosynthesis systems, and combination mammography/tomosynthesis systems. The system flexibly supports the use of any mode of image capture (i.e., scout, two dimensional mammogram, three-dimensional reconstructed volume) for either or both target visualization and target localization. With such an arrangement, a needle biopsy assembly having improved patient coverage is provided for use with a variety of different x-ray imaging platforms.

Having described exemplary embodiments, it can be appreciated that the examples described above are only illustrative and that other examples also are encompassed within the scope of the appended claims.

What we claim is:

1. A needle biopsy assembly for an imaging system, the needle biopsy assembly comprising:
    a support structure comprising a first side and a second side;
    at least one handle extending from the support structure;
    a coupling mechanism extending from the first side of the support structure, wherein the coupling mechanism is configured to couple the needle biopsy assembly to the imaging system;
    a guidance module extending from the second side of the support structure;
    a fixed support arm extending from the guidance module; and
    an angular support arm coupled to the fixed support arm at an angle offset from a plane defined by the support structure.

2. The needle biopsy assembly of claim 1 further comprising a holster mount, moveably coupled to the angular support arm, the holster mount adapted to support a needle biopsy holster along the angular support arm.

3. The needle biopsy assembly of claim 2 wherein the guidance module further comprises components for controlling a motorized movement of the holster mount along the angular support arm.

4. The needle biopsy assembly of claim 2 further comprising a mechanism for manually advancing the holster mount along the angular support arm.

5. The needle biopsy assembly of claim 2 further comprising a control unit for controlling the guidance module.

6. The needle biopsy assembly of claim 5 wherein the control unit includes a display for displaying information related to the biopsy assembly.

7. The needle biopsy assembly of claim 6 wherein the information is associated with a position of a biopsy device coupled to the angular support arm.

8. The needle biopsy assembly of claim 6 wherein the information includes information associated with a type of biopsy device coupled to the angular support arm.

9. The needle biopsy assembly of claim 5 wherein the display information includes warning information related to the biopsy assembly.

10. The needle biopsy assembly of claim 1 including an adjustment mechanism for adjusting the angle between the fixed support and the angular support arm.

11. The needle biopsy assembly of claim 1 further comprising a needle support coupled to the angular support arm.

12. The needle biopsy assembly of claim 1 further comprising a lateral biopsy arm, couplable to the assembly, for supporting a biopsy needle during lateral biopsies.

13. A needle biopsy assembly for an imaging system, the needle biopsy assembly comprising:
    a support structure comprising a first side and a second side;
    a pair of handles extending from the support structure;
    a fixed support arm extending from the first side of the support structure;
    an angular support arm extending from the fixed support arm at an angle offset from a plane defined by the support structure;
    a connector pivotably securing the angular support arm to the fixed support arm;
    an adjustment mechanism for varying an angle of displacement between the angular support arm and the fixed support arm; and
    a plurality of hooks extending from the second side of the support structure, wherein the hooks are configured to removably connect the needle biopsy assembly to the imaging system.

14. The needle biopsy assembly of claim 13, further comprising a holster mount movably coupled to the angular support arm.

15. The needle biopsy assembly of claim 14, further comprising an attachment mechanism for securing a biopsy holster to the angular support arm.

16. The needle biopsy assembly of claim 13, further comprising a lateral biopsy arm removably securable to the angular support arm.

17. A needle biopsy assembly for an imaging system, the needle biopsy assembly comprising:
    a support structure;
    a first handle extending from a first end of the support structure;
    a second handle extending from a second end of the support structure;
    a guidance module secured to the support structure between the first handle and the second handle;
    a fixed support arm extending from the guidance module;
    an angular support arm extending from the fixed support arm at an angle offset from a plane defined by the support structure;
    a display removably positionable to each of the first handle and the second handle; and
    a coupling mechanism extending from the support structure, wherein the coupling mechanism is configured to couple the needle biopsy assembly to the imaging system.

18. The needle biopsy assembly of claim 17, wherein the angular support arm is pivotably connected to the fixed support arm.

\* \* \* \* \*